United States Patent [19]

Doi et al.

[11] 4,314,048
[45] Feb. 2, 1982

[54] ALIPHATIC TRIISOCYANATE, A METHOD FOR PREPARING IT AND THE PREPARATION OF POLYURETHANE RESINS THEREWITH

[75] Inventors: Tsunesuke Doi, Tama; Akira Ide, Nobeoka; Yasushi Kishimoto, Nobeoka, all of Japan

[73] Assignee: Asahi Kasei Kogyo Kabushiki Kaisha, Japan

[21] Appl. No.: 236,544

[22] Filed: Feb. 20, 1981

[30] Foreign Application Priority Data

Mar. 11, 1980 [JP] Japan .................................. 55-29751

[51] Int. Cl.³ .................... C08G 18/00; C07C 119/042
[52] U.S. Cl. ............................. 528/44; 260/453 PH; 260/453 AL
[58] Field of Search ................. 260/453 AL, 453 PH; 528/44

[56] References Cited

U.S. PATENT DOCUMENTS

| | | | |
|---|---|---|---|
| 2,865,940 | 12/1958 | Nobis et al. | 260/453 PH |
| 3,218,345 | 11/1965 | Rainer | 260/453 AL |
| 3,487,050 | 12/1969 | Castro et al. | 528/44 X |
| 3,631,198 | 12/1971 | Horvitz | 260/453 PH |
| 3,631,201 | 12/1971 | Farrissey et al. | 260/465 H |
| 4,107,199 | 8/1978 | Konig et al. | 260/465 D |
| 4,276,228 | 6/1981 | Nishino et al. | 260/453 AL |

FOREIGN PATENT DOCUMENTS

| | | |
|---|---|---|
| 13493 | 7/1980 | European Pat. Off. |
| 55-327 | 1/1980 | Japan |
| 55-90526 | 7/1980 | Japan |

OTHER PUBLICATIONS

Derwent Publication Accession No. 251C, published 2/13/80.

Primary Examiner—Dolph H. Torrence
Attorney, Agent, or Firm—Finnegan, Henderson, Farabow, Garrett & Dunner

[57] ABSTRACT

4-Isocyanate methyl-1,8-octamethylene diisocyanate of the formula (I),

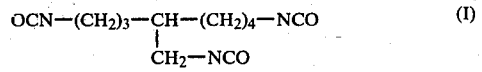

and a method of preparing 4-isocyanate methyl-1,8-octamethylene diisocyanate of the formula (I) which comprises reacting 4-aminomethyl-1,8-diaminooctane of the formula (II),

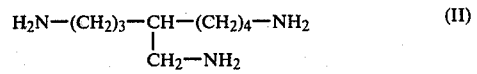

or its salt with phosgene at a temperature of about 70° C. to about 220° C. in an inert reaction medium.

5 Claims, No Drawings

ALIPHATIC TRIISOCYANATE, A METHOD FOR PREPARING IT AND THE PREPARATION OF POLYURETHANE RESINS THEREWITH

BACKGROUND OF THE INVENTION

1. Field of the Invention

This invention relates to a novel aliphatic triisocyanate, a method of its preparation and a hardener for a non-yellowing polyurethane resin comprising the aliphatic triisocyanate.

2. Description of the Prior Art

It is known that aliphatic polyisocyanates can be employed as starting materials for producing non-yellowing polyurethane resins having good weatherability. Exemplary aliphatic polyisocyanates of non-yellowing type include hexamethylene diisocyanate, 2,2,4- and 2,4,4-trimethylhexamethylene diisocyanate. These diisocyanates, however, have irritant odor at ordinary temperature and toxicity to human bodies and thus disadvantageously it is difficult to safely handle these diisocyanates. Accordingly, they are employed in the form of their adducts by reacting the diisocyanates with a diol such as ethylene glycol and butanediol or a triol such as trimethylolpropane as a so-called agent for producing the adduct. But the adducts become polymer mixtures having a high viscosity and should be diluted with a solvent from the standpoint of their easy handling.

SUMMARY OF THE INVENTION

The present invention, in one aspect, provides 4-isocyanate methyl-1,8-octamethylene diisocyanate (hereinafter referred to "triisocyanate") of the formula (I),

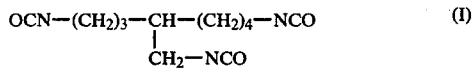

$$OCN-(CH_2)_3-\underset{\underset{CH_2-NCO}{|}}{CH}-(CH_2)_4-NCO \quad (I)$$

In a second aspect, this invention provides a method of preparing the triisocyanate of the formula (I) which comprises reacting 4-aminomethyl-1,8-diaminooctane (hereinafter referred to "triamine") of the formula (II),

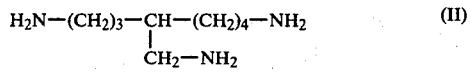

$$H_2N-(CH_2)_3-\underset{\underset{CH_2-NH_2}{|}}{CH}-(CH_2)_4-NH_2 \quad (II)$$

or its salt with phosgene.

In a third aspect, this invention provides a hardener for a non-yellowing polyurethane resin comprising the triisocyanate of the formula (I) as the main component.

DETAILED DESCRIPTION OF THE INVENTION

The triamine of the formula (II) which is employed as the starting material for preparing the triisocyanate of the formula (I) in this invention is a known compound and can be prepared by convention methods, for example, by trimerizing acrylonitrile by electrolytic reduction or amalgam reduction to give 1,3,6-tricyanohexane and catalytically hydrogenating 1,3,6-tricyanohexane in the presence of a catalyst [see Japanese Patent Application (OPI) No. 5903/1979].

The triisocyanate of the formula (I) can be prepared by directly reacting the triamine of the formula (II) with phosgene in an inert reaction medium or by dissolving or suspending the salt of the triamine of the formula (II) in an inert reaction medium and reacting the obtained solution or suspension with phosgene.

Exemplary salts which can be employed in this invention include the hydrochloride, carbonate, sulfate, phosphate and acetate.

The mol ratio of phosgene to the triamine or its salt which can be employed in this invention is theoretically at least 3, typically at least about 5 and preferably ranges from about 5 to about 90. A more preferred mol ratio of phosgene to the triamine or its salt ranges from about 15 to about 45.

The inert reaction medium which can be employed in this reaction may be any reaction medium which can be employed in the conventional phosgenation, more specifically, which does not react with the starting materials i.e., the triamine or its salt and phosgene and the reaction product, which sufficiently dissolves the starting materials and phosgene and which scarcely dissolves evolving hydrogen chloride.

Exemplary inert reaction media include aliphatic hydrocarbons such as octane, nonane, 2,2,5-trimethylhexane and decane; aromatic hydrocarbons such as toluene, xylene, ethylbenzene, cumene, mesitylene, tetraline, butylbenzene, diethylbenzene and pentylbenzene; chlorinated aliphatic hydrocarbons such as 1,1,1,2-tetrachloroethane, 1,1,2,2-tetrachloroethane, pentachloroethane, hexachloroethane and 1,2,3-trichloropropane; chlorinated aromatic hydrocarbons such as monochlorobenzene, o-dichlorobenzene, m-dichlorobenzene, 1,2,4-trichlorobenzene, o-chlorotoluene, p-chorotoluene and 1-chloronaphthalene; and chlorinated alicyclic hydrocarbons such as chlorocyclohexane. Of these compounds, monochlorobenzene, o-dichlorobenzene, 1,2,4-trichlorobenzene and tetraline are preferred.

The amount of the inert reaction medium which can be employed in this invention varies depending upon the triamine or its salt chosen and is at least about 200 parts by weight and typically ranges from about 200 parts by weight to about 5,000 parts by weight based on 100 parts by weight of the triamine or its salt. A preferred amount of the inert reaction medium ranges from about 500 parts by weight to about 3,000 parts by weight based on 100 parts by weight of the triamine or its salt.

The reaction temperature which can be employed in this invention is typically from about 70° C. to about 220° C.

In the present invention, the reaction pressure can be either atmospheric or a pressure above atmospheric, preferably ranging from atmospheric to about 50 Kg/cm².

The period of reaction may vary within wide limits depending upon the triamine or its salt selected, the pressure and temperature chosen and other factors. Generally, however, the reaction period ranges from about 20 minutes to about 30 hours.

The method of this invention will now be explained in more detail.

When the triamine is employed as the starting material and reacted with phosgene in an inert reaction medium, the triamine is firstly converted into the counterpart carbamyl chloride (first step) and secondly the formed carbamyl chloride is converted into the triisocyanate (second step). The reaction temperature of the first step may be the same as that of the second step but it is preferred that the reaction temperature of the first step is lower than that of the second step by about 50° C. to about 100° C. and that the reaction temperature of the second step, i.e., is about 120° C. to about 200° C.

On the other hand, when the triamine in the form of the salt is employed as the starting material, it is preferred that the salt is firstly finely pulverized and secondly is suspended in the inert reaction medium or that an inert reaction medium capable of dissolving the salt is firstly selected and secondly the salt of the triamine is dissolved therein. Then phosgene is introduced into the obtained suspension or solution while the temperature of the suspension or solution is preferably maintained at about 120° C. to about 200° C. When the temperature is above about 200° C., formation of resinous materials is increased and accordingly, the yield of the desired material is decreased. On the other hand, when the temperature is below about 120° C., the reaction is retarded and completion of the reaction requires a long period of time.

After the reaction is completed, the inert reaction medium is removed from the reaction solution by distillation and the remaining product is subjected to distillation under reduced pressure to give the pure triisocyanate of this invention, i.e., 4-isocyanate methyl-1,8-octamethylene diisocyanate. When any hydrolyzable chlorine component still remains in the triisocyanate, powder of a metal such as copper, zinc and iron or a base such as calcium oxide is added to the triisocyanate and the mixture is subjected to heat treatment at about 80° C. to about 200° C. and then to rectification to remove the hydrolyzable chlorine component.

The triisocyanate thus obtained is a novel compound having a boiling point of 161°-163° C./1.2 mmHg which is odorless, colorless liquid at 25° C.

The chemical structure of the triisocyanate can be confirmed mainly by spectral analyses such as infrared absorption spectral analysis, NMR spectral analysis and mass spectral analysis. More specifically, the infrared absorption spectrum shows an absorption at 2230 cm$^{-1}$ due to the reverse stretching vibration of the isocyanate groups and absorptions at 2925, 2850, 1465 and 1335 cm$^{-1}$ due to the methylene groups. The NMR spectrum shows an absorption of proton in the methylene groups centering around about 1.5 ppm and an absorption of proton linking with the carbon having an isocyanate group centering around about 3.3 ppm. The integral of each of these absorption peaks is proportional to the corresponding number of protons. The mass spectrum shows a parent peak at m/e=251 corresponding to the molecular weight and a characteristic peak at m/e=195 corresponding to

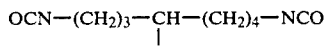

OCN—(CH$_2$)$_3$—CH—(CH$_2$)$_4$—NCO
| fragment formed by scission of the triisocyanate. By these spectral analyses the structure of the triisocyanate according to this invention can be proved to be the above described formula (I).

Furthermore, by elemental analysis the calculated values obtained from the above described formula (I) is identical with the found values. Also, when the reaction product of the triisocyanate with n-dibutylamine is subjected to back titration with a hydrochloric acid solution, the NCO content is identical with the theoretical amount. Each chart by gas chromatography and liquid chromatography shows a single peak, respectively, and any peak due to impurities cannot be recognized. By the above described various analyses it is confirmed that the above described formula (I) is correct and that the triisocyanate of this invention is a single compound.

The triisocyanate of this invention has a remarkable low viscosity, i.e., about 5 cp at 25° C. and a low vapor pressure and does not substantially have irritant odor at ordinary temperature. Thus, the triisocyanate can be easily and safely handled.

The triisocyanate of this invention is especially useful as a hardener for preparing non-yellowing polyurethane resins. The triisocyanate as such is not only stable to heat and light but also imparts resistance to light and weatherability to polyurethane resins obtained by using the triisocyanate. For example, polyurethane coated films prepared from the triisocyanate do not show any change when exposed outdoors for at least one year and are excellent. Further, since the triisocyanate has a very low vapor pressure and no irritant odor at ordinary temperature compared with conventional aliphatic diisocyanate, e.g., hexamethylene diisocyanate, the triisocyanate can be safely used without forming its adduct. The triisocyanate which has one more isocyanate group in the molecule shows sufficient cross-linkability as the hardener for polyurethane resins. Also the triisocyanate may also be used as its adduct with any agent for forming the adduct such as a diol and a triol.

The NCO content of the triisocyanate is as high as 50% weight and accordingly, the triisocyanate can impart excellent properties to the articles deriving therefrom in a comparatively small amount. Furthermore, since the triisocyanate is colorless liquid and has a very low viscosity at ordinary temperature compared with all-purpose aliphatic polyisocyanate adducts such as hexamethylene diisocyanate biuret (trademark "Desmodur N", product of Farbenfabriken Bayer A.G.) and hexamethylene diisocyanate/trimethylolpropane adduct (trademark "Coronate HL", product of Nippon Polyurethane Co., Ltd.), it is unnecessary to dilute the triisocyanate with a solvent for the purpose of easy handling. Thus the triisocyanate can be preferably employed as a hardener for polyurethane resins containing solids in a greater amount. The triisocyanate can be easily purified by distillation to give the pure triisocyanate.

The triisocyanate of this invention is very useful as the starting material for preparing polyurethane resins and can be employed in preparing, for example, coating materials, elastomers, foams, adhesives and films. Especially the triisocyanate can be preferably used as a hardener for preparing non-yellowing polyurethane resins.

More specifically, non-yellowing polyurethane resins can be prepared by reacting the triisocyate of this invention with at least one organic compound having at least two reactive hydrogen-containing groups as determined by the Zerewitinoff at a ratio of the reactive hydrogen: the mol of the isocyanate group being about 0.2 to about 5:1 and preferably about 0.8 to about 1.2:1.

Exemplary organic compounds having at least two reactive hydrogen-containing groups includes (1) hydroxyl group-containing compounds such as (a) diols such as ethylene glycol, propylene glycol, 1,4-butylene glycol, 1,3-butylene glycol, polyethylene glycol and polypropylene glycol; (b) polyols such as glycerine, trimethylolpropane, pentaerythritol and sorbitol; (c) polyester polyols such as polyether polyols having a molecular weight of about 500 to about 100,000 obtained by addition reaction of at least one polyhydric alcohol such as glycerine and propylene glycol to at least one alkylene oxide such as ethylene oxide, propylene oxide and 1,2-butylene oxide, polyether polyols obtained by reaction of an alkylene oxide with a polyfunctional compound such as ethylene diamine and ethanolamine and polytetramethylene glycols obtained by ring-opening polymerization of tetrahydrofuran; (d) polyester polyols such as polyester polyols having a molecular weight of about 500 to about 100,000 obtained by condensation reaction of at least one dicarboxylic acid such as succinic acid, adipic acid, sebacic acid, dimeric acid, maleic anhydride, phthalic anhydride, isophthalic acid and terephthalic acid with at least one polyhydric alcohol such as ethylene glycol, propylene glycol, diethylene glycol, butylene glycol, neopentyl glycol, trimethylolpropane and glycerine; (e) acrylic polyols such as acrylic polyols having a molecular weight of about 500 to about 100,000 obtained by polymerizing at least one acrylate or methacrylate having at least one hydroxyl group in the molecule such as 2-hydroxyethyl acrylate, hydroxypropyl acrylate, 2-hydroxyethyl methacrylate and hydroxypropyl methacrylate and at least one acrylate or methacrylate such as methyl acrylate, ethyl acrylate, isopropyl acrylate, n-butyl acrylate, 2-ethylhexyl acrylate, methyl methacrylate, ethyl methacrylate, isopropyl methacrylate, n-butyl methacrylate, isobutyl methacrylate, n-hexyl methacrylate and lauryl methacrylate in the presence or absence of at least one compound selected from unsaturated carboxylic acids such as acrylic acid, methacrylic acid and itaconic acid, unsaturated amides such as acrylamide, N-methylolacrylamide and diacetone acrylamide and other polymerizable monomers such as styrene, glycidyl methacrylate, vinyltoluene, acrylonitrile; (2) other hydroxyl group-containing compounds such as polybutadienes having at least two terminal hydroxyl groups, polythioether polyols, polythioester polyols, polyacetal polyols, polycarbonate polyols and polyesteramide polyols; and (3) any mixtures of at least one hydroxyl group-containing compound as described above with at least one compound having at least two reactive hydrogen containing groups selected from (a) primary or secondary amino group-containing compounds such as diamines such as ethylenediamine, trimethylenediamine, 1,2-diaminopropylenediamine, tetramethylenediamine, hexamethylenediamine, 1,4-diaminocyclohexane, xylylenediamine, trimethylhexamethylenediamine, diaminodiphenylmethane and isophoronediamine, polyamines such as diethylenetriamine, triethylenetetramine, polyamines obtained by addition reaction of at least one alkylene polyamine such as diethylenetriamine and triethylenetetramine with at least one alkylene oxide such as ethylene oxide and propylene oxide and other modified polyamines, (b) carboxyl group-containing compounds such as liquid polybutadienes having at least two terminal carboxyl groups, (c) thiol group-containing compounds such as dithiols such as ethanediol and, 1,4-butanediol, polythiols such as trithioglycerine, polyether polythiols obtained by addition reaction of at least one polythiol with at least one alkylene oxide and polythioester polythiols obtained by condensation reaction of at least one dicarboxylic acid with at least one polythiol and (d) epoxy group-containing compounds such as epoxy resins having a molecular weight of about 500 to about 100,000 such as novolac type, epichlorohydrin type, cyclic oxirane type, glycidyl ether type, glycidyl ester type, polyglycol ether type, glycol ether type, epoxidated aliphatic unsaturated compound type, epoxidated fatty acid ester type, polycarboxylic acid ester type, aminoglycidyl type or resorcin type epoxy resins.

In preparing polyurethane coating material composition, the triisocyanate of this invention and the above described organic compounds having at least two reactive hydrogen-containing groups are dissolved in an inert organic solvent such as ethyl acetate, butyl acetate, cellosolve acetate, methyl formamide, diethyl ether of diethylene glycol, methyl ethyl ketone, methyl isobutyl ketone, benzene, toluene, xylene and benzine.

The polyurethane resins obtained by using the triisocyanate of this invention have excellent weatherability, stability to light, resistance to water, resistance to chemicals and resistance to soiling and the coated films have good quick drying, hardness and adhesion.

The present invention will now be illustrated in greater detail with reference to several Examples, but they are given for illustrative purposes only and are not to be construed as limiting the invention.

EXAMPLE 1

In 145 g of methanol were dissolved 106 g of the triamine and to the solution were added dropwise 175 ml of 35% concentrated hydrochloric acid under cooling in such a manner that the temperature did not exceed 30° C. Then the reaction mixture was concentrated by removing methanol and water under reduced pressure and added with 1000 ml of acetone and further the concentration of the mixture was continued to give a viscous triamine hydrochloride. This triamine hydrochloride was finely pulverized and dried at 60° C./5 mmHg for 10 hours.

In a 1 l four necked flask equipped with a stirrer, a gas inlet, a reflux condenser and a thermometer were charged 65 g of the fine power of the triamine hydrochloride and 480 g of tetraline as the solvent. When the temperature of the solution was raised to 120° C. with sufficient stirring, the introduction of phosgene into the solution at rate of 20 g/hour was initiated and the temperature was increased to and maintained at 185° C. and phosgene was continuously passed into the solution for 14 hours. The reaction solution was gradually colored and when the introduction of phosgene was stopped the color of the reaction solution was brown. The reaction solution was cooled and then the phosgene dissolved in the reaction solution was removed at a reduced pressure of 50 mmHg in a nitrogen gas stream and further tetraline was distilled off under reduced pressure to give a crude triisocyanate. On distilling this crude triisocyanate under vacuum, there were obtained 42.0 g of colorless transparent 4-isocyanate methyl-1,8-octamethylene diisocyanate having a boiling point of 161°–163° C./1.2 mmHg (yield: 72%). The analytical values of this triisocyanate are as follows;

Viscosity: 5.0 cp at 25° C.
NCO content: 50.0 weight % (theoretical amount: 50.2 weight %)
Refractive index: $n_D^{20}$ 1.4740
Density: 1.052 at 20° C.
Elemental analysis for $C_{12}H_{17}N_3O_3$: Calculated (%): C: 57.4, H: 6.8, N: 16.7; Found (%): C: 57.2, H: 6.8, N: 16.6
Infrared absorption spectrum: 2925, 2850, 2230, 1465, 1335 cm$^{-1}$ Mass spectrum: m/e=251 (corresponding to the molecular weight);

m/e =
195 [corresponding to OCN—(CH$_2$)$_3$—CH—(CH$_2$)$_4$—NCO]
                                          |

NMR spectrum: ($^1$H-60 MHz, solvent CD$_3$COCD$_3$, reference TMS, temperature 25° C.)
1.5, 3.3 ppm

EXAMPLE 2

In a 10 l four necked flask equipped with a stirrer, a gas inlet, a reflux condenser and a thermometer were charged 300 g of the triamine and 5000 g of o-chlorobenzene. While the inner temperature of the flask was maintained at 70° C. to 80° C., phosgene was introduced into the solution at a rate of 130 g/hour and white precipitates began to form. After the continuous introduction of phosgene there was obtained a yellow carbamyl chlorinated suspension. Then the temperature of the suspension was raised to 160° C. and phosgene was further passed into the suspension at a rate of 60 g/hour for 12 hours. After a small amount of precipitates was removed from the obtained brown reaction solution, the phosgene dissolved in the reaction solution was removed at a temperature of 70° C. to 80° C. under a reduced pressure of 10 to 20 mmHg and then o-chlorobenzene was distilled off under a reduced pressure of at most 1 mmHg. Further the brown residue was distilled under reduced pressure to give 320 g of pale yellow crude triisocyanate having a boiling point of 165°-168° C./1.5 mmHg (yield: 74%).

To this triisocyanate were added 20 g of copper powder and while the temperature of the mixture was maintained at 165° C., dry nitrogen gas was passed into the mixture at a rate of 5 l/hour for 2 hours to rectify the crude triisocyanate, resulting in 231 g of colorless transparent 4-isocyanate methyl-1,8-octamethylene diisocyanate having a boiling point of 158°-159° C./1.0 mmHg. The analytical values of this triisocyanate are as follows;

Viscosity: 5.0 cp at 25° C.
NCO content: 50.1 weight % (theoretical amount: 50.2 weight %)
Refractive index: n$_D^{20}$ 1.4741
Elemental analysis for C$_{12}$H$_{17}$N$_3$O$_3$: Calculated (%): C: 57.4, H: 6.8, N: 16.7; Found (%): C: 57.3, H: 6.8, n; 16.6
Infrared absorption spectrum: 2925, 2850, 2230, 1465, 1335 cm$^{-1}$
Mass spectrum: m/e=251 (corresponding to the molecular weight)

m/e =
195 [corresponding to OCN—(CH$_2$)$_3$—CH—(CH$_2$)$_4$—NCO]
                                          |

NMR spectrum: ($^1$H-60 MHz, solvent CD$_3$COCD$_3$, reference TMS, temperature 25° C.)
1.5, 3.3 ppm

EXAMPLE 3

In a 2 l four necked flask equipped with a stirrer, a gas inlet, a reflux condenser and a thermometer were charged 120 g of the triamine and 800 g of tetraline and into the mixed solution was passed dry carbon dioxide gas at a rate of about 500 ml/minute for 3 hours at 25° C. to give a viscous suspension of the triamine carbonate.

When the temperature of this suspension was increased the triamine carbonate was completely dissolved at about 90° C. to form a homogeneous solution. The temperature was further increased and the introduction of phosgene into the solution was initiated at 120° C. at a rate of 30 g/hour and the temperature was increased to 185° C. over a period of 5 hours. Then phosgene was further passed into the reaction solution while the temperature of the reaction solution was maintained at 185° C. The reaction solution was gradually colored and was brown at the stoppage of the introduction of phosgene.

The obtained reaction solution was cooled and then the phosgene dissolved in the reaction solution was removed at a reduced pressure of 50 mmHg in a nitrogen gas stream and further tetraline was distilled off under reduced pressure to give a crude triisocyanate. On distilling this crude triisocyanate, there were obtained 42.0 g of colorless transparent 4-isocyanate methyl-1,8-octamethylene diisocyanate having a boiling point of 161°-163° C./1.2 mmHg (yield: 72%).

Viscosity: 5.1 cp at 25° C.
NCO content: 50.1 weight % (theoretical amount: 50.2 weight %)
Refractive index: n$_D^{20}$ 1.4740
Density: 1.053 at 20° C.
Elemental analysis for C$_{12}$H$_{17}$N$_3$O$_3$: Calculated (%): C: 57.4, H: 6.8, N: 16.6; Found (%): C: 57.4, H: 6.8, N: 16.6
Infrared absorption spectrum: 2925, 2850, 2230, 1465, 1335 cm$^{-1}$
Mass spectrum: m/e=251 (corresponding to the molecular weight)

m/e =
195 [corresponding to OCH—(CH$_2$)$_3$—CH—(CH$_2$)$_4$—NCO]
                                          |

NMR spectrum: ($^1$H-60 MHz, solvent CD$_3$COCD$_3$, reference TMS, temperature 25° C.)
1.5, 3.3 ppm

EXAMPLE 4

A two-liquid type polyurethane coating material was prepared by mixing, as the component A, the triisocyanate having a NCO content of 50.1 weight % as obtained in Example 2 with, as the component B, an acrylic polyol having 50 weight % of non-volatiles and a hydroxyl value of solids of 100 (trademark "Acrydic A-801", manufactured by Dainippon Ink & Chemicals, Inc.) at a NCO/OH mol ratio of 1/1 and diluting the mixture with a mixed solvent of ethyl acetate/toluene/butyl acetate in a 30/30/20 weight ratio to such an extent that the solids content was adjusted by Ford cup #4 in accordance with the method of JIS K 5402.

The obtained coating material was coated on an iron sheet, a tinplate sheet, an aluminum sheet and glass sheet, respectively, in such a manner that the thickness of the coated film was 50μ with an air spray gun having a nozzle diameter of 10 mm (Type W-61, manufactured by Iwata Painting Machine Industry Co., Ltd.), hardened at 20° C. at a relative humidity of 60%, set at 20° C. at a relative humidity of 60% and baked at 120° C.

for 60 minutes. The properties of the coated films were measured and the results are set forth in Table below.

COMPARATIVE EXAMPLES 1 AND 2

The same procedures as Example 4 were repeated except that Desmodur N (product of Farbenfabriken Bayer Aktiengesellschaft) and Coronate HL (product of Nippon Polyurethane Co., Ltd.) were employed as the component A, respectively. The properties of the coated films are set forth in Table.

TABLE

|  | Example No. | Comparative Examples Nos. | |
|---|---|---|---|
|  | 4 | 1 | 2 |
| Coating Material Composition | | | |
| Component A | Triisocyanate of this invention | Desmodur N | Coronate HL |
| Component B | Acrydic A-801 | Acrydic A-801 | Acrydic A-801 |
| Solids Content at Coating*[1] (weight %) | 35 | 31 | 30 |
| Pot Life*[2] (hour) | 15 | 50 | 42 |
| Hardening Time*[3] (hour) | 10 | 42 | 29 |
| Properties of Coated Film | | | |
| Pencil Hardness*[4] | | | |
| 1 day after | 3B | <6B | <6B |
| 2 days after | HB | <6B | 6B |
| 3 days after | F | 5B | 3B |
| 5 days after | F | HB | HB |
| 7 days after | H | F | F |
| Du Pont Impact Strength*[4] (cm) (500 g × ½ inch) | 50 (satisfactory) | 50 (satisfactory) | 50 (satisfactory) |
| Adhesion (to Iron)*[5] | 100/100 | 100/100 | 100/100 |
| Frichsen*[6] (mm) | at most 8 | at most 8 | at most 8 |
| Bending*[4] | pass | pass | pass |
| Resistance to Hot Water at 40° C. for 24 hours*[4] | ◎ | ○ | ○ |
| Resistance to Chemicals at 20° C. for 24 hours*[7] | | | |
| Toluene | ○ | ○ | ○ |
| Methyl ethyl ketone | ○ | Δ | ○ |
| Cellosolve acetate | ○ | ○ | ○ |
| Gasoline | ◎ | ◎ | ◎ |
| Gloss (60* mirror plane)*[4] | 91 | 93 | 89 |
| External Appearance*[8] | ◎ | ◎ | ◎ |
| Weather-O-Meter Yellowing Degree*[9] (Δ Yellowless Index) | | | |
| 200 hours | 0.5 | 0.6 | 0.6 |
| 500 hours | 1.7 | 1.9 | 2.0 |
| 1000 hours | 3.8 | 4.2 | 4.0 |
| External Appearance after One Year Outdoor Exposure*[8] | ◎ | ◎ | ◎ |

Note:
*[1]JIS K 5402 (Ford cup #4: 20 seconds/25° C.)
*[2]Period of time for fluidity to cease to exist
*[3]Period of time at 20° C. at a relative humidity of 60%
*[4]JIS K 5400
*[5]JIS D 0202
*[6]JIS Z 2247
*[7]In the manner described in JIS K 5400 : no change, ○: softened, Δ: slightly swollen
*[8] : good
*[9]JIS K 7103

As is understood from the above described Table, use of the triisocyanate of this invention could provide a coating material composition having a high solids concentration at the time of its application and there could be obtained a coated film having excellent hardening property at ordinary temperature, good hardness, adhesion and resistance to chemicals and superior weatherability.

While the invention has been described in detail and with reference to specific embodiments thereof, it will be apparent to one skilled in the art that various changes and modifications can be made therein without departing from the spirit and scope thereof.

What is claimed is:

1. 4-Isocyanate methyl-1,8-octamethylene diisocyanate of the formula (I),

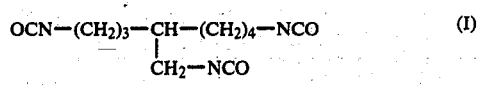

(I)

2. A method of preparing 4-isocyanate methyl-1,8-octamethylene diisocyanate of the formula (I) which comprises reacting 4-aminomethyl-1,8-diaminooctane of the formula (II),

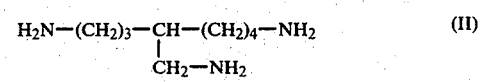

(II)

or its salt with phosgene at a temperature of about 70° C. to about 220° C. in an inert reaction medium.

3. The method of claim 2, wherein the salt is the hydrochloride, the carbonate, the sulfate, the phosphate or the acetate.

4. In a method of preparing a non-yellowing polyurethane resin by the reaction of an organic polyisocyanate and an organic compound having at least two reactive hydrogen-containing groups as determined by the Zerewitinoff method, the improvement which comprises employing 4-isocyanate methyl-1,8-octamethylene diisocyanate of claim 1 as the polyisocyanate.

5. The method of claim 4, wherein the 4-isocyanate methyl-1,8-octamethylene diisocyanate is reacted with the organic compound having at least two reactive hydrogen-containing groups as determined by the Zerewitinoff method at a ratio of the reactive hydrogen: the mol of the isocyanate group being about 0.2 to about 5:1.

* * * * *